United States Patent
Hirayama et al.

(10) Patent No.: US 6,570,390 B2
(45) Date of Patent: May 27, 2003

(54) METHOD FOR MEASURING SURFACE LEAKAGE CURRENT OF SAMPLE

(75) Inventors: Taisei Hirayama, Akishima (JP); Koichiro Ito, Osaka (JP); Ryo Hattori, Tokyo (JP); Yoshitsugu Yamamoto, Tokyo (JP); Yoshihiro Notani, Tokyo (JP); Shinichi Miyakuni, Tokyo (JP)

(73) Assignees: Rigaku Corporation, Tokyo (JP); Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/941,903

(22) Filed: Aug. 29, 2001

(65) Prior Publication Data

US 2002/0030504 A1 Mar. 14, 2002

(30) Foreign Application Priority Data

Aug. 29, 2000 (JP) ........................................ 2000-259869

(51) Int. Cl.⁷ .............................................. G01R 31/00
(52) U.S. Cl. ....................................... 324/501; 250/306
(58) Field of Search ................................ 324/501, 751; 250/306

(56) References Cited

U.S. PATENT DOCUMENTS 4,912,052 A * 3/1990 Miyoshi ..................... 324/751
5,097,204 A * 3/1992 Yoshizawa .................. 324/751
5,393,980 A * 2/1995 Yost ........................... 250/306
5,543,334 A * 8/1996 Yoshii ........................ 324/769

FOREIGN PATENT DOCUMENTS

JP       7-301648       11/1995

* cited by examiner

Primary Examiner—Christine K. Oda
(74) Attorney, Agent, or Firm—Frishauf, Holtz, Goodman & Chick, P.C.

(57) ABSTRACT

A method of measuring a surface leakage current includes applying a voltage between a pair of electrodes, which are apart from each other on a sample surface, during a predetermined period of time. A region of the sample surface between the pair of electrodes is irradiated by energy rays during an irradiation period of time which is within the voltage application time. The energy rays may be lasers, ultraviolet rays, X-rays or an electron beam. A current flowing between the pair of electrodes is measured during the voltage application time. The energy rays irradiation causes a surface leakage current, which is caused by adhered substances, to start to flow, and when the adhered substances have been eliminated perfectly, a relatively large current caused by the adhered substances disappears. Perfect elimination of the adhered substances can be verified by confirming that the relatively large current has disappeared.

9 Claims, 3 Drawing Sheets

METHOD FOR MEASURING SURFACE LEAKAGE CURRENT OF SAMPLE

BACKGROUND OF THE INVENTION

This invention relates to a method for measuring a surface leakage current of a sample.

The electric resistance of a sample surface (i.e., surface resistance) can be measured in a manner that a voltage is applied between a pair of electrodes (which may include a combination of a central circular electrode and a ring electrode surrounding it) on the sample surface and then a current, which flows between these electrodes, is measured.

In such measurement of the sample surface resistance, if there are adhered substances on the sample surface, a leakage current caused by the adhered substances is disadvantageously to be measured as included in the total current. The leakage current caused by the adhered substances becomes error in measuring accurately an essential current flowing through the sample per se. Accordingly, cleaning of the sample surface is required in measuring accurately the sample surface resistance. The cleaning method may be performed by using cleaning solution or heating in a vacuum vessel to eliminate the adhered substances.

In cleaning the sample surface prior to the measurement, an operator might be concerned about if the adhered substances have been removed at all. That is, when the surface resistance is measured after the cleaning of a sample, an operator might be concerned about if the measurement result is for the ideal condition in which the adhered substances have been removed at all. If the operator wants, before measurement of the surface resistance, to confirm reliably if the adhered substances have been removed at all, suitable testing facilities and testing operation are required.

The measurement technique for the surface leakage current of a sample is not restricted to the above-mentioned sample surface resistance measurement but can be used in various situations. For example, in a TSC (Thermally Stimulated Current) method in which a current flowing through a sample is measured as the sample temperature varies, the adhered substances have an influence on the TSC measurement which measures a current flowing through the surface of a sample. Therefore, in such a TSC measurement, it is necessary to measure the surface leakage current under the ideal condition that the adhered substances have been removed from the sample surface. Other than the TSC, similarly in measurement means such as DEA (Dielectric Analysis: thermal relaxation measurement), DLTS (Deep Level Transient Spectroscopy), ICTS (Isothermal Capacitance Transient Spectroscopy), TSIC (Thermally Stimulated Ionic Current) IV (Current-Voltage characteristic) and CV (Capacitance-Voltage characteristic), it is preferable that the surface leakage current is measured iunder the ideal condition that the adhered substances have been removed. It is noted that all of these measurement means such as TSC, DEA, DLTS, ICTS, IV and CV belong to "a thermoelectric analyzer for measuring the thermoelectric property of a sample as the sample temperature varies".

SUMMARY OF THE INVENTION

It is an object of the invention to provide a method for measuring accurately a surface leakage current of a sample without separate facilities for removing the adhered substances from the sample surface beforehand.

It is another object of the invention to provide a method for measuring a surface leakage current wherein perfect elimination of the adhered substances from the sample surface can be verified.

A method of measuring a surface leakage current according to the invention has the steps of voltage application, energy rays irradiation and current measurement. The step of voltage application applies a voltage between a pair of electrodes, which are apart from each other on a sample surface, during a predetermined voltage application period of time. The step of energy rays irradiation irradiates, by energy rays, a region of the sample surface between the pair of electrodes during a predetermined irradiation period of time which is within the voltage application period of time. The energy rays may be lasers, ultraviolet rays, X-rays or an electron beam. The step of current measurement measures a current flowing between the pair of electrodes during the voltage application period of time.

With this method, the energy rays irradiation makes a surface leakage current, which is caused by adhered substances, start to flow, and when the adhered substances have been eliminated perfectly a relatively large current caused by the adhered substances disappears. Therefore, the adhered substances can be removed at the same time that the surface leakage current is measured. Furthermore, perfect elimination of the adhered substances can be verified by confirming that a relatively large current has disappeared. This method of measuring a surface leakage current can be performed with the use of "a thermoelectric analyzer for measuring the thermoelectric property of a sample as the sample temperature varies". In that case, if the surface leakage current is measured prior to the measurement of the thermoelectricity of a sample, adhered substances can be removed from the sample surface; besides, perfect elimination of the adhered substances can be verified.

With this invention, the adhered substances can be removed without separate facilities for removing the adhered substances from the sample surface beforehand but with the use of the measurement device for the surface leakage current as it is. Besides, perfect elimination of the adhered substances can be verified electrically.

DETAILED DESCRIPTION OF THE PREFERRED EMBODIMENTS

Figure 1:
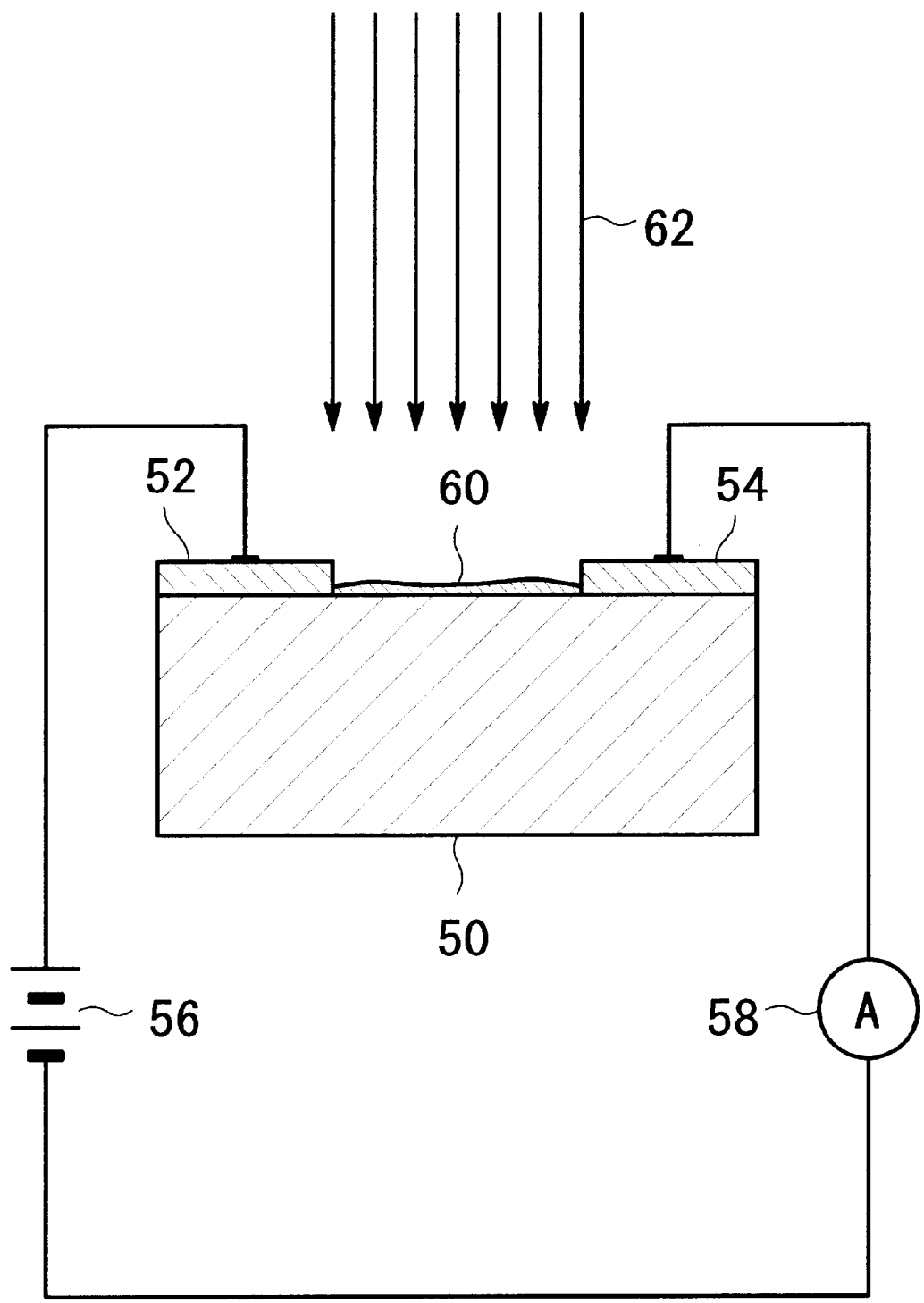
FIG. 1 is a cross-sectional elevation showing the principle of a method for measuring the surface leakage current according to the invention.

First of all, the principle of the method for measuring the surface leakage current according to the invention will be explained by reference to FIG. 1. A sample 50 has a surface on which a pair of electrodes 52 and 54 are formed. Between the electrodes 52 and 54 are connected a voltage source 56 and an ammeter 58 in series. There are a certain amount of substances 60 adhered on a region of sample surface between the electrodes 52 and 54. When the region of the sample surface between the electrodes 52 and 54 is exposed to energy rays 62 during voltage application, the adhered substances 60 are eliminated from the sample surface.

Measuring a current flowing between the electrodes 52 and 54 by the ammeter 58, a surface leakage current flowing through the adhered substances 60 can be observed during existence of the adhered substances 60. When the adhered substances 60 have been eliminated perfectly, the surface leakage current caused by the adhered substances 60 disappears. Accordingly, perfect elimination of the adhered substances 60 can be verified at the time of disappearance of the surface leakage current caused by the adhered substances 60. Thereafter, the exposure to the energy rays 62 is terminated and an essential surface leakage current of the sample per se can be measured. Hence it is possible to remove the adhered substances from the sample surface with the sample held in the condition for the measurement of the essential surface leakage current of the sample per se, resulting in quick transfer to the essential measurement with the sample as it is. Furthermore, the perfect disappearance of the adhered substances can be verified.

Figure 2:
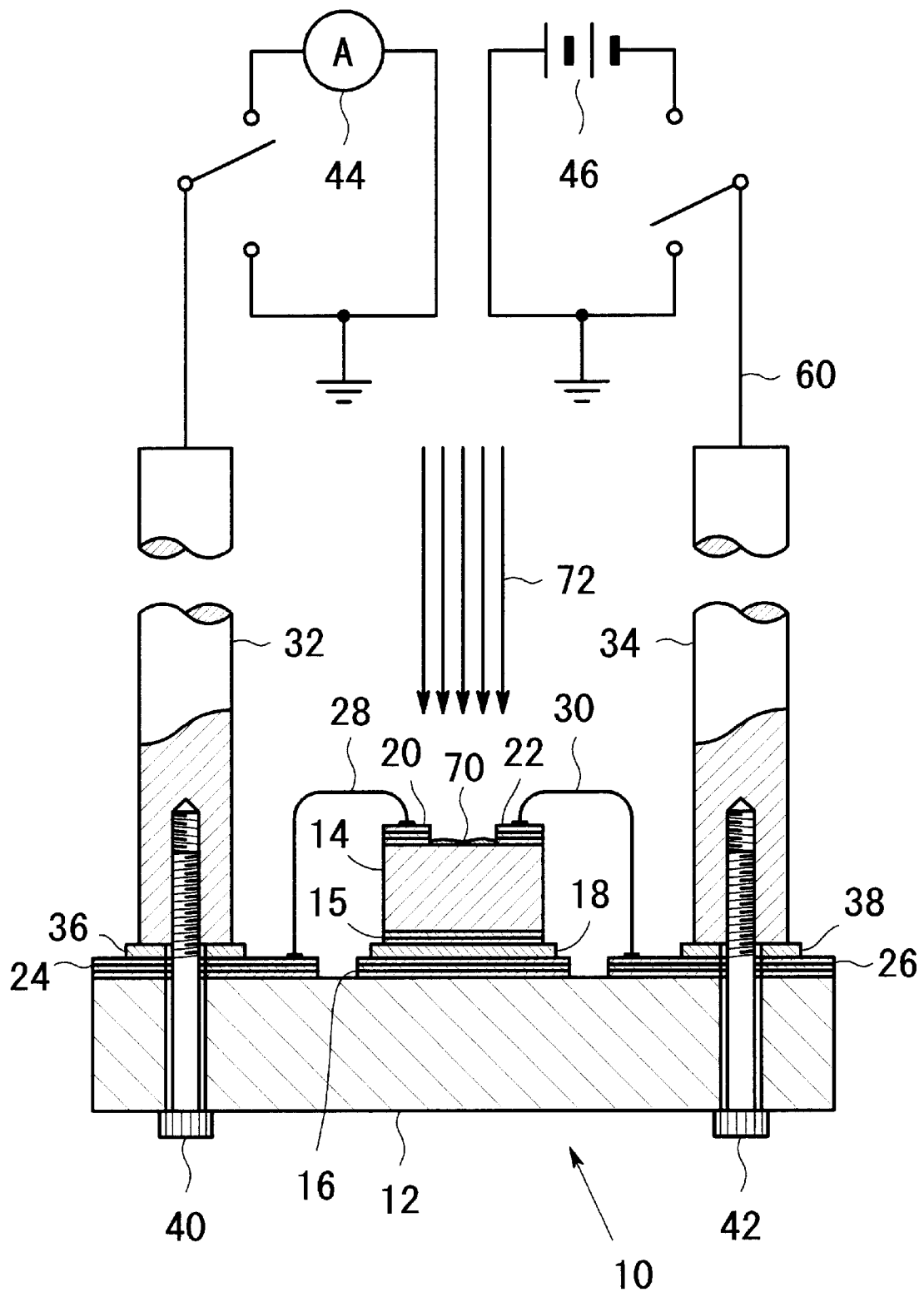
FIG. 2 is a cross-sectional elevation showing one embodiment of the method for measuring the surface leakage current according to the invention which is applied to a sample of a TSC method.

FIG. 2 is a cross-sectional elevation showing one embodiment of the method for measuring the surface leakage current according to the invention which is applied to a sample of a TSC method. The sample assembly shown in the figure includes a substrate 12 made of aluminum nitride to which a GaAs sample 14 is bonded. The long substrate 12 has a longitudinally-central region, on which an intermediate layer 16 is deposited by vacuum evaporation. The intermediate layer 16 is made of a multilayer having a three-layered structure of Ti/Mo/Au. That is, Ti (titanium), Mo (molybdenum) and Au (gold) are deposited in the described order from the substrate side. The substrate 12 has the two longitudinally-end regions, on which a pair of junction electrode layers 24 and 26 are deposited by vacuum evaporation with certain distances from the central intermediate layer 16. Each of these junction electrode layers 24 and 26 also is made of a multilayer having a three-layered structure of Ti/Mo/Au similarly to the central intermediate layer 16. On the intermediate layer 16 is bonded the GaAs sample 14 via an adhesive layer 18 which is made of In (indium).

The sample 14 has the bottom surface covered with a two-layered film 15 which consists of Ti (titanium) and Au (gold) layers in the described order from the sample side. Accordingly, at the region at which the sample 14 is bonded to the substrate 12, layers of Ti/Mo/Au/In/Au/Ti are to be arranged, in the described order from the substrate side, between the aluminum nitride substrate 12 and the GaAs sample 14.

The sample 14 has the top surface on which a pair of electrode layers 20 and 22 are deposited by vacuum evaporation with a distance therebetween. Each of the electrode layers 20 and 22 is made of a multilayer which has a three-layered structure of AuGe/Ni/Au, that is, layers of 88%Au-12%Ge (gold-germanium) alloy, Ni (nickel) and Au (gold) are deposited in the described order from the sample side.

The sample 14 has, on its surface, the left electrode layer 20 having the top layer (Au) which is electrically connected to the top layer (Au) of the left junction electrode layer 24 via two Au wires 28. Similarly, the sample 14 has, on its surface, the right electrode layer 22 having the top layer (Au) which is electrically connected to the top layer (Au) of the right junction electrode layer 26 via other two Au wires 30.

The sample assembly 10 is supported, in a TSC analyzer, by two support rods 32 and 34 made of stainless steel. These support rods 32 and 34 serve also as conductors for making an electric circuit. The left support rod 32 is joined to the substrate 12 of the sample assembly 10 by a screw 40. A gold washer 36 is inserted between the bottom surface of the support rod 32 and the top surface of the left junction electrode 24. The support rod 32 has a lower portion having an internal thread with which the screw 40 can engage. The right support rod 34 is similarly joined to the substrate 12 by another screw 42 and another Au washer 38. The substrate 12 has, near its center, a hole (not shown) into which a platinum resistance thermometer (or a thermocouple) is inserted.

Between the pair of support rods 32 and 34 are selectively connected an ammeter 44 and a voltage source 46. Lead cables 60, which are connected with the support rods 32 and 34, are triple-shielded cables, expecting noise reduction.

Since the sample assembly 10 includes the sample 14 having the top surface on which the pair of electrode layers 20 and 22 are formed, a thermally stimulated current along the surface of the sample 14 can be measured. That is, the sample assembly 10 enables crystal defect analysis in the vicinity of the sample surface.

Figure 3:
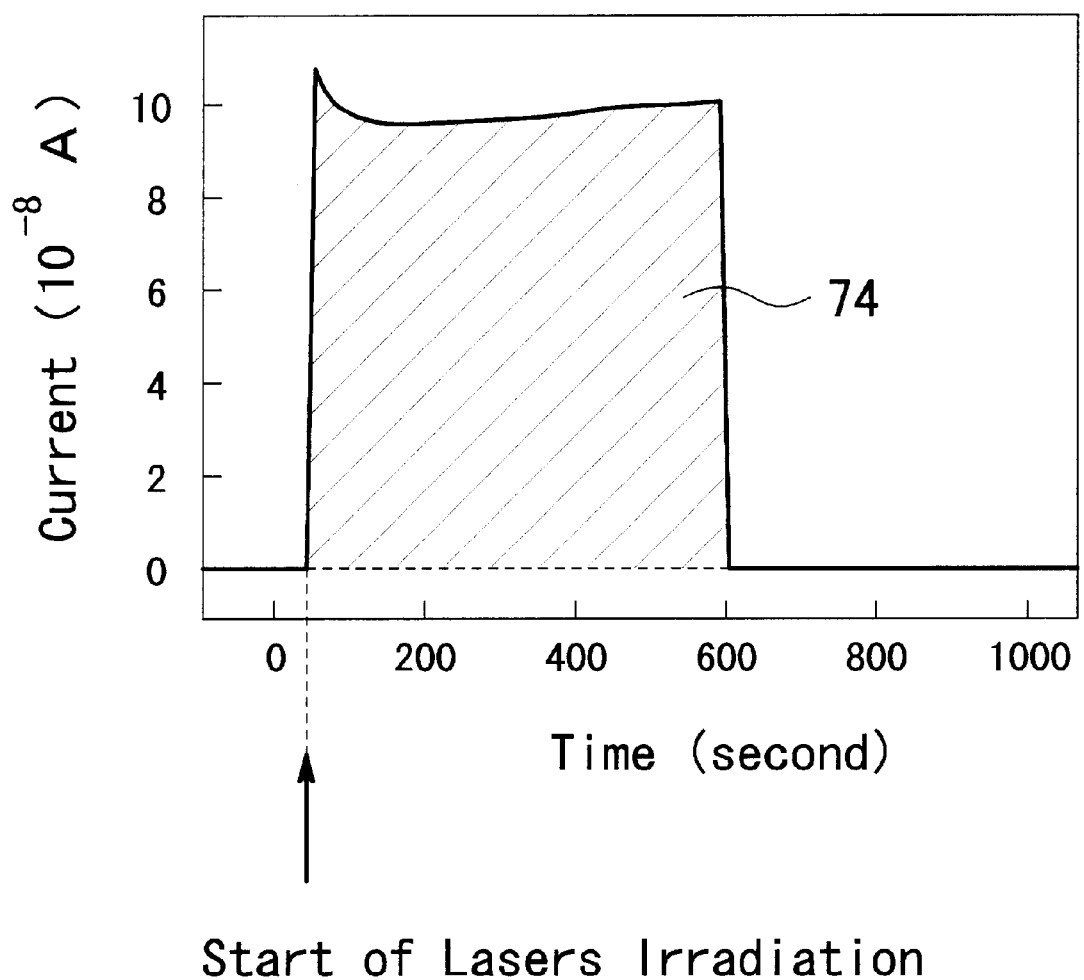
FIG. 3 is a graph showing an elimination step of the adhered substances with the use of the sample assembly shown in FIG. 2.

Prior to the TSC measurement with the use of this sample assembly, the sample 14 is first exposed to lasers 72 to eliminate the adhered substances 70 from the sample surface. FIG. 3 is a graph showing an elimination step of the adhered substances with the use of the sample assembly shown in FIG. 2. The abscissa represents a time and the ordinate represents a current flowing between the pair of support rods 32 and 34. At the time of zero, a voltage is applied between the pair of electrodes 32 and 34 and thereafter the lasers 72 irradiate the region of the sample surface between the pair of electrode layers 20 and 22, resulting in a rapid increase in current immediately after the irradiation. Thereafter, a certain amount of current flows for a while: that is, a relatively large current flows for a certain period of time (about ten minutes in this graph) and then the current is decreased rapidly to almost zero, noting that in this graph the lasers irradiation continues until a thousand seconds elapse.

The sample may be high-purity compound semiconductor. A high-purity GaAs sample has relatively high electric resistance at a low temperature, so that the surface leakage current such as shown in the graph does not flow for this sample per se. Therefore, the surface leakage current appearing in the graph is equal to the current caused by substances adhered on the sample surface. As can be seen from the graph, with the ten-minute lasers irradiation, perfect disappearance of the adhered substances 70, from the region of the sample surface between the pair of electrode layers 20 and 22, can be verified. Hence, if the TSC measurement of the sample 14 is carried out after the verification, high-accuracy measurement can be made without the influence of the adhered substances.

The area of the hatching region 74 in the graph of FIG. 3 is proportional to an amount of the adhered substances which have been eliminated from the sample. Accordingly, with calculating this area in the graph, the amount of the adhered substances which have been in existence between the pair of electrodes can be grasped. With this grasp, there is a further advantage that a large-or-small relationship, among plural samples, of the adhered substances on the sample surfaces can be judged. Calculating the area of the region 74 is, in other words, the integration of the surface leakage current (obtaining an integrated value) during the period of time from the start of flow of the surface leakage current to its disappearance.

What is claimed is:

1. A method for measuring a surface leakage current of a sample, comprising:
   (a) applying a voltage between a pair of electrodes, which are apart from each other on a surface of said sample, during a predetermined voltage application period of time;
   (b) irradiating a region of said sample surface between said pair of electrodes with energy rays during a predetermined irradiation period of time which is within said voltage application period of time; and
   (c) measuring a current flowing between said pair of electrodes during said voltage application period of time,
   wherein said surface leakage current is measured using a thermoelectric analyzer which measures an electric property of said sample as a sample temperature varies.

2. A method according to claim 1, wherein said surface leakage current is measured to verify perfect elimination of adhered substances from said sample surface prior to measurement of said electric property of said sample by said thermoelectric analyzer.

3. A method according to claim 2, wherein said thermoelectric analyzer comprises a thermally stimulated current analyzer.

4. A method according to claim 3, wherein said surface leakage current is integrated during a period of time from start of flow of said surface leakage current to disappearance of said surface leakage current, and an amount of substances adhered to said sample surface is determined based on said integrated value.

5. A method according to claim 4, wherein said energy rays comprise laser beams.

6. A method according to claim 1, wherein said thermoelectric analyzer comprises a thermally stimulated current analyzer.

7. A method according to claim 1, wherein said sample comprises a high-purity compound semiconductor.

8. A method according to claim 1, wherein said surface leakage current is integrated to obtain an integrated value during a period of time from start of flow of said surface leakage current to disappearance of said surface leakage current, and an amount of substances adhered to said sample surface is determined based on said integrated value.

9. A method according to claim 1, wherein said energy rays comprise laser beams.

* * * * *